United States Patent [19]

Frank et al.

[11] Patent Number: 4,492,804

[45] Date of Patent: Jan. 8, 1985

[54] PREPARATION OF PRIMARY AMINES

[75] Inventors: Gerhard Frank, Hirschberg; Peter Rudolf, Neuhofen; Gerald Neubauer, Weinheim; Paul Duffner, Ludwigshafen; Manfred Ohlinger, Frankenthal; Hans J. Wilfinger; Emil Pfannebecker, both of Schifferstadt, all of Fed. Rep. of Germany

[73] Assignee: BASF Aktiengesellschaft, Fed. Rep. of Germany

[21] Appl. No.: 524,318

[22] Filed: Aug. 18, 1983

[30] Foreign Application Priority Data

Aug. 21, 1982 [DE] Fed. Rep. of Germany ....... 3231193

[51] Int. Cl.³ .............................................. C07C 85/12
[52] U.S. Cl. .................................................. 564/493
[58] Field of Search ........................................ 564/493

[56] References Cited

U.S. PATENT DOCUMENTS

| 2,165,515 | 7/1939 | Schmidt | 564/493 |
| 3,062,869 | 11/1962 | Gould | 564/493 X |
| 3,152,184 | 10/1964 | Levering | 564/493 X |
| 4,003,933 | 1/1977 | Drake | 564/493 X |
| 4,036,883 | 7/1977 | Voges et al. | 564/493 X |
| 4,254,059 | 3/1981 | Grey et al. | 564/493 X |

FOREIGN PATENT DOCUMENTS

| 1072972 | 1/1958 | Fed. Rep. of Germany | 564/493 UX |
| 1061760 | 3/1963 | Fed. Rep. of Germany | 564/493 UX |
| 1259899 | 6/1968 | Fed. Rep. of Germany | 564/493 UX |
| 2034380 | 5/1973 | Fed. Rep. of Germany | 564/493 UX |
| 2429293 | 9/1977 | Fed. Rep. of Germany | 564/493 UX |
| 1317464 | 5/1973 | United Kingdom | 564/493 |
| 1486890 | 9/1977 | United Kingdom | 564/493 |
| 1539436 | 1/1979 | United Kingdom | 564/493 |
| 1539437 | 1/1979 | United Kingdom | 564/493 |

Primary Examiner—Paul F. Shaver
Attorney, Agent, or Firm—Keil & Weinkauf

[57] ABSTRACT

Saturated primary amines are prepared by reacting a nitrile with hydrogen at elevated temperature under superatmospheric pressure in the presence of ammonia and a metallic iron catalyst which has been obtained by reducing anisometric iron oxide particles with hydrogen at not more than 500° C.

8 Claims, No Drawings

PREPARATION OF PRIMARY AMINES

Cobalt-containing catalysts are preferably used for preparing amines by hydrogenation of nitriles, for example hexamethylenediamine from adiponitrile, because of their high selectivity. German Pat. Nos. 1,072,972 and 1,259,899, for example, disclose such processes. However, the life of the cobalt catalysts used no longer corresponds to industrial requirements, and in addition findings indicate that dusts of metallic cobalt and its sparingly soluble compounds should be avoided for industrial hygiene reasons. Iron-containing catalysts have also been previously used for hydrogenating nitriles to amines. However, higher temperatures must be used in this case, which leads to increased formation of by-products. In the preparation of hexamethylenediamine, for example, azacycloheptane and diamines which are difficult to separate off from the hexamethylenediamine, such as 2-aminomethylcyclopentylamine and 1,2-diaminocyclohexane, as well as bis-hexamethylenetriamine are formed. German Laid-Open application DOS No. 2,429,293 thus discloses that a catalyst which achieves a selectivity of from 98 to 99% for hexamethylenediamine at hot-spot temperatures of from 150° to 170° C. is achieved by melting magnetite and reducing it with hydrogen. However, the 1,2-diaminocyclohexane content is 0.2% by weight. Even in the process described in German Published application DAS No. 2,034,380, in which a granular iron compound which has been converted into metallic iron by reduction with water is used as the catalyst, selectivities of from only 97 to 98.8% by weight are achieved. Such iron catalysts do not yet meet all the expectations of industry and are therefore in need of improvement.

It is an object of the present invention to provide iron catalysts which have a long life in the hydrogenation of nitriles to amines, permit lower hydrogenation temperatures, produce few by-products and have a high selectivity.

We have found that this object is achieved by a process for the preparation of saturated primary amines by reacting a nitrile with hydrogen at elevated temperature under superatmospheric pressure in the presence of ammonia and a metallic iron catalyst which has been obtained by reducing an iron compound with hydrogen at $\leq 500°$ C., wherein a metallic iron catalyst which has been obtained from anisometric iron oxide particles is used.

The novel process has the advantage that the catalyst used has a long life and still has superior properties even after prolonged use, and also the advantage that a high selectivity is achieved at lower hydrogenation temperatures. Moreover, fewer by-products which are difficult to separate off from the useful products are obtained.

Preferred starting substances are aliphatic, cycloaliphatic, araliphatic or aromatic nitriles of not more than 20 carbon atoms. One or more nitrile groups can be present in the molecule. Saturated or olefinically unsaturated nitriles are suitable for the hydrogenation. They can also carry substituents which are inert under the reaction conditions, such as alkyl of 1 to 4 carbon atoms which is bonded via an ether bridge. Alkanenitriles and alkanedinitriles of 3 to 18 carbon atoms are particularly preferred starting substances, suitable examples being propionitrile, acetonitrile, acrylonitrile, benzyl cyanide, benzonitrile, glutarodinitrile and adipodinitrile.

The process has achieved particular industrial importance in the hydrogenation of adipodinitrile to hexamethylenediamine.

The reaction is generally carried out under pressures of from 100 to 400 bar, preferably 200 to 300 bar, and advantageously at from 80° to 140° C., preferably from 100° to 120° C.

The reaction is carried out in the presence of ammonia, advantageously in a volume ratio of nitrile to ammonia of from 1:2 to 1:20, preferably from 1:6 to 1:12. It is also possible to replace some of the ammonia by recycled crude hydrogenation mixture, which consists substantially of amine and ammonia.

An iron catalyst which has been obtained by reducing anisometric iron oxide particles with hydrogen at $\leq 500°$ C. is used according to the invention. The degree of reduction of the metallic iron particles is advatageously $\geq 95\%$. Degree of reduction is understood as meaning the amount of available iron in % present in metallic form. Anisometric $\gamma$-iron oxides, especially $\gamma$-iron-III oxide and $\gamma$-iron-III oxide hydroxide, are preferably used as the starting substances. $\gamma$-Iron-III oxide hydroxide, which is known by the name lepidocrocite, is preferred. It can be obtained, for example, by the process described in German Published application DAS No. 1,061,760. The anisometric iron oxides have, for example, an average particle length of from 0.1 to 2 m$\mu$, preferably from 0.2 to 1.2 m$\mu$, with a length : thickness ratio of from 5:1 to 40:1, and a specific surface area, measured by the BET method, of from 25 to 80 m$^2$/g. The annealed products of the above iron-III oxides can also similarly be used. Annealing is advantageously carried out at from 250° to 700° C. The iron oxide particles preferably have an alkali content of <0.1% by weight, calculated as sodium oxide.

The metallic iron catalysts according to the invention can be used as a suspension, but molded catalyst masses which additionally contain lubricants, e.g. inorganic materials having a lattice structure, such as talc or, in particular, graphite, are preferably used. Molded catalysts advantageously contain from 1 to 5% by weight of lubricant, based on the total catalyst material of iron particles and lubricant. Graphite has proved to be a particularly suitable lubricant. The molded iron catalyst material thus consists substantially of metallic iron particles, small amounts of iron oxide, depending on the degree of reduction of the iron particles, and a lubricant. The molded iron catalyst material, for example in the form of beads, tablets or strands, advantageously has a compressive strength of $\geq 300$ kp/cm$^2$.

The molded iron catalyst materials preferably used are advantageously prepared from, for example, $\gamma$-iron-III oxides, in particular $\gamma$-iron-III oxide hydroxide (lepidocrocite). The annealed products of the above iron-III oxides, annealing advantageously being carried out at from 250° to 700° C., can also be used in a similar manner. Iron-III oxide hydroxide is obtained, for example, from aqueous solutions of iron salts by precipitation with sodium hydroxide solution by a process such as that described in German Published application DAS No. 1,061,760. The $\gamma$-iron oxide hydroxide particles are advantageously washed until the alkali content is <0.1% by weight, calculated as sodium oxide. The needle-shaped iron-III oxide particles are reduced by means of hydrogen in a fluidized bed, in a rotating tube oven or, preferably, in a stirred fixed bed at from 260° to 500° C., in particular from 300° to 450° C., in the course of from 3 to 36 hours. A dried stream of hydrogen is advantageously used, a relatively high flow rate being maintained. Not less than a 60-fold excess of hydrogen has proved suitable. The reduction is advantageouly carried out until the degree of reduction is ≧95%. The needle-shaped metal particles thus obtained, which consist substantially of iron, still have to a great extent the shape of the starting substances, and are homogeneous in spite of the preceeding conversion reaction.

The resulting metal particles are then stabilized, which means coating them with a layer of oxide by controlled oxidation in order to eliminate pyrophoric properties caused by the large free surface area of the small particles. This coating is achieved by passing an air/nitrogen mixture over the metal powder while maintaining exactly a temperature which preferably does not exceed 100° C., in particular 80° C. After the stabilization, the degree of reduction should be not less than 80%, preferably not less than 90%. The stabilized iron particles have a surface area, measured by the BET method, of from 4 to 25 m²/g, preferably from 8 to 12 m²/g, lengths of from 0.05 to 2.0 mμ and pore volumes of less than 0.4 cm³/g, the ratio of micropores to macropores being in favor of the macropores in the range of from 1:6 to 1:10.

The iron particles thus stabilized are mixed with an inert lubricant, preferably graphite, advantageously in an amount of from 2 to 5% by weight. The mixture of stabilized iron particles and lubricants is advantageously processed to give moldings, for example pressed into tablets, under a blanket of nitrogen. The compressive strength of the moldings should be ≧300 kp/cm². The moldings thus obtained are activated by treatment with a relatively large excess, for example a 60-fold excess, of hydrogen at ≦500° C., preferably at from 300° to 460° C., under atmospheric or superatmospheric pressure, e.g. from 100 to 150 bar. The degree of reduction thereby achieved should advantageously be ≧95%. The compressive strength of the moldings is increased, for example from 300 to 600–800 kg/cm², by the activation.

The nitriles can be hydrogenated batchwise or, advantageously, continously, for example in a trickle procedure on fixed-bed molded iron catalysts.

The amines which can be obtained by the process according to the invention can be used for the preparation of stabilizers. Hexamethylenediamine, which is obtained by the process according to the invention, is an important starting material for the preparation of nylon-6,6.

The Examples which follow illustrate the process according to the invention.

EXAMPLE 1

Preparation of the catalyst 600 kg of needle-shaped lepidocrocite (γ-FeOOH), which has a chlorine content of <0.1% and an Na₂O content of <0.1%, is prepared as described in German Published application DAS No. 1,061,760 and has a specific surface area of 32 m²/g, an average needle length of 0.8 mμ, a length/thickness ratio of the needles of 22:1, a bulk density of 0.37 g/cm³ and a pH of 7.2, are reduced into metallic iron (Fe≧95%) with 400 m³ (S.T.P.)/hour of hydrogen in a stirred fixed bed at 400° C. for 38 hours (stoichiometric excess of hydrogen: 64). The pyrophoric needle-shaped metallic pigment is then coated with a stabilizing layer of oxide in a nitrogen/air mixture at 60° C., during which the degree of reduction should not fall below 90%. The yield is 400 kg. The saturation magnetization of the iron particles is 153 nT m³/g in a measurement field of 160 kA/M. The iron particles have a specific surface area, measured by the BET method, of 7.2 m²/g and, when viewed under an electron microscope, have an anisotropic geometric shape (needle or rod shape).

To produce molded materials 5 mm in diameter and 4 mm in height, the stabilized pulverulent metal pigment is mixed with 2% by weight of graphite and the mixture is tableted under a blanket of nitrogen. The compressive strength of the tablets should be not less than 300 kp/cm².

EXAMPLE 2

350 liters of the moldings thus prepared are introduced into a reactor 1,800 mm in length and with an internal diameter of 160 mm and are treated with a large excess of hydrogen at 360° C. under 150 bar for 24 hours for the purpose of activation. The hydrogen is thereby circulated via a condenser for deposition of the water of reduction.

After the catalyst has been cooled, the reactor is charged, by the trickle procedure under a hydrogen pressure of 270 bar, with a mixture of 85 liters/hour of adipodinitrile and 510 liters/hour of liquid ammonia, the hydrogen being circulated (400 m³ (S.T.P.)/hour). The temperature of the feed mixture is 78° C. and that of the reactor discharge is 110° C.; hot-spot temperatures of not more than 119° C. result.

Analysis of the crude hexamethylenediamine by gas chromatography after evaporating off the ammonia from the hydrogenation mixture shows 0.02% by weight of hexylamine, 0.09% by weight of azacycloheptane, 0.11% by weight of 1,2-diaminocyclohexane, 99.78% by weight of hexamethylenediamine and an aminocapronitrile content of 0.01%. There is 0.36% distillation residue, consisting predominantly of bishexamethylenetriamine. The selectivity is calculated as 99.4% for hexamethylenediamine. After an operating time of 300 days, the catalyst has the same activity and selectivity without any regeneration.

EXAMPLE 3

70 liters/hour of adipodinitrile are reacted in 430 liters/hour of liquid ammonia and 490 liters/hour of recycled hydrogenation mixture over the catalyst prepared according to Example 1 and in the reactor described under Example 2 to give hexamethylenediamine. A pressure of 250 bar of hydrogen and 350 m³ (S.T.P)/hour of circulation gas are maintained. Complete conversion of the adipodinitrile is achieved at a feed temperature of 77° C., the reactor discharge temperature being 104° C. and the maximum temperature in the reactor being 109° C.

Analysis of the crude hexamethylenediamine by gas chromatography after evaporation of the ammonia shows 0.01% of hexylamine, 0.05% of azacycloheptane, 0.11% of 1,2-diaminocyclohexane, 0.002% of 2-aminomethylcyclopentylamine, 99.80% of hexamethylenediamine and 0.01% of aminocapronitrile. There is 0.40% of distillation residue and the selectivity is calculated as 99.44% for hexamethylenediamine.

EXAMPLE 4

3 liters of the catalyst prepared according to Example 1 are introduced into a high-pressure reactor 2,000 mm in length and having an internal diameter of 45 mm, and the catalyst is activated as in Example 2. 100 ml/hour of adipodinitrile and 1,200 ml/hour of liquid ammonia are metered into the reactor. A selectivity of 99.63% for hexamethylenediamine is achieved at a hydrogenation temperature of 109° C. under a pressure of 260 bar. The crude hexamethylenediamine contains only 0.04% of azacycloheptane and 0.09% of 1,2-diaminocyclohexane. There is 0.23% of distillation residue.

EXAMPLE 5

80 g of 2-methylglutarodinitrile and 100 ml of liquid ammonia are hydrogenated in the presence of 80 g of catalyst tablets, prepared as in Example 1, under 260 bar at 100° C. in a 2 liter shaken autoclave until no more hydrogen is taken up. A selectivity of 98.8% for 2-methyl-pentamethylenediamine is achieved, with complete conversion of the dinitrile employed.

Propionitrile is hydrogenated to n-propylamine in liquid ammonia with a selectivity of 97.5% under hydrogenation conditions similar to those above.

EXAMPLE 6

The procedure is as described in Example 4, except that 3 liters of catalyst which has been prepared by tableting a mixture of 98% of γ-FeOOH and 2% of graphite are introduced into the reactor. The catalyst is reduced by means of hydrogen under atmospheric pressure at 450° C. for 72 hours. A degree of reduction of 95% is achieved. A hydrogenation temperature of 155° C. under 260 bar is necessary for complete conversion of 400 g/hour of adipodinitrile in 1,460 g/hour of $NH_3$ (trickle procedure). The selectivity of the catalyst is 97.15% for hexamethylenediamine. The crude hexamethylenediamine contains 1.56% of products which have reacted too far and 1.29% of cyclic products (1,2-diaminocyclohexane and azacycloheptane).

EXAMPLE 7

The procedure is as described in Example 4, except that 3 liters of a catalyst which has been prepared by reducing α-FeOOH and tableting the resulting iron metal particles, after rendering the surface passive and mixing with 2% of graphite, are used. Since the α-FeOOH was precipitated in the alkaline range, 0.18% of sodium hydroxide is incorporated in the catalyst. The catalyst is activated by treatment with hydrogen under atmospheric pressure at 360° C. for 24 hours. 400 g/hour of adipodinitrile and 1,460 g/hour of $NH_3$ are then metered in, in a trickle procedure.

Complete conversion of the adipodinitrile is achieved at 172° C. The selectivity is 97.8% for hexamethylenediamine, 1.3% of cyclic by-products and 0.8% of products which have reacted too far (predominantly bishexamethylenediamine) being obtained.

We claim:

1. A process for the preparation of a saturated primary amine by reacting a nitrile with hydrogen at elevated temperature under superatmospheric pressure in the presence of ammonia and a metallic iron catalyst which has been obtained by reducing an iron compound with hydrogen at $\leq 500°$ C., wherein a metallic iron catalyst which has been obtained from anisometric iron oxide particles is used.

2. The process of claim 1, wherein the iron oxide particles used contain less than 0.1% by weight of alkali, calculated as sodium oxide.

3. The process of claim 1, wherein anisometric γ-iron-III oxide hydroxide is used as the starting substance.

4. The process of claim 1, wherein molded iron catalyst materials which have been obtained by reducing anisometric γ-iron oxide particles to metallic iron particles with hydrogen at from 250° to 500° C., stabilizing the resulting metallic iron particles by treatment with a mixture of nitrogen and air, pressing the stabilized iron particles to moldings, together with lubricants, and activating the moldings by treatment with hydrogen at $\leq 500°$ C. are used.

5. The process of claim 1, wherein the molded iron catalyst material contains from 1 to 5% by weight of graphite, as a lubricant.

6. The process of claim 1, wherein the moldings have a compressive strength greater than 300 $kp/cm^2$.

7. The process of claim 1, wherein the anisometric γ-iron oxide particles are reduced to a degree of reduction of $\geq 95\%$.

8. The process of claim 1, wherein an alkanenitrile or alkanedinitrile of 3 to 18 carbon atoms is used as the starting substance.

* * * * *